United States Patent
Sur et al.

(10) Patent No.: US 9,498,583 B2
(45) Date of Patent: Nov. 22, 2016

(54) FROTH DETECTION SYSTEM AND METHOD

(71) Applicants: Kunal Sur, Evanston, IL (US); Paul T. Kotnik, Commerce Township, MI (US); Anatoly S. Belkin, Glenview, IL (US); John Hicks Dumas, III, Libertyville, IL (US); Timothy L. Ruchti, Gurnee, IL (US)

(72) Inventors: Kunal Sur, Evanston, IL (US); Paul T. Kotnik, Commerce Township, MI (US); Anatoly S. Belkin, Glenview, IL (US); John Hicks Dumas, III, Libertyville, IL (US); Timothy L. Ruchti, Gurnee, IL (US)

(73) Assignee: Hospira, Inc., Lake Forest, IL (US)

( * ) Notice: Subject to any disclaimer, the term of this patent is extended or adjusted under 35 U.S.C. 154(b) by 701 days.

(21) Appl. No.: 13/630,031

(22) Filed: Sep. 28, 2012

(65) Prior Publication Data

US 2013/0085689 A1    Apr. 4, 2013

Related U.S. Application Data

(60) Provisional application No. 61/460,766, filed on Sep. 30, 2011.

(51) Int. Cl.
*A61M 5/36* (2006.01)
*A61M 1/36* (2006.01)
*G06F 19/00* (2011.01)
*A61M 5/142* (2006.01)

(52) U.S. Cl.
CPC .......... *A61M 5/365* (2013.01); *A61M 1/3626* (2013.01); *G06F 19/3481* (2013.01); *A61M 5/142* (2013.01); *A61M 2205/3375* (2013.01)

(58) Field of Classification Search
CPC .................................................. A61M 1/3626
See application file for complete search history.

(56) References Cited

U.S. PATENT DOCUMENTS

| | | | |
|---|---|---|---|
| 4,068,521 A | 1/1978 | Cosentine et al. | |
| 4,764,166 A | 8/1988 | Spani | |
| 4,981,467 A * | 1/1991 | Bobo, Jr. ............ | A61M 5/365 604/122 |
| 5,176,631 A | 1/1993 | Koenig | |
| 5,180,287 A | 1/1993 | Natwick et al. | |
| 5,392,638 A | 2/1995 | Kawahara | |
| 5,394,732 A | 3/1995 | Johnson et al. | |
| 5,505,696 A | 4/1996 | Miki | |
| 5,616,124 A | 4/1997 | Hague | |
| 6,142,008 A | 11/2000 | Cole et al. | |
| 2005/0192529 A1* | 9/2005 | Butterfield et al. ............ | 604/65 |
| 2009/0053071 A1* | 2/2009 | Wang et al. .................... | 417/12 |
| 2010/0280430 A1 | 11/2010 | Caleffi et al. | |
| 2011/0160649 A1 | 6/2011 | Pan | |

OTHER PUBLICATIONS http://www.merriam-webster.com/dictionary/froth, accessed on May 13, 2015.*
ttp://www.diffen.com/difference/Continually_vs_Continuously retrieved by archive.org on Aug. 13, 2009.*
International Search Report, PCT/US12/57878, Jan. 7, 2013.

* cited by examiner

*Primary Examiner* — Paul D Lee
*Assistant Examiner* — Mark Crohn
(74) *Attorney, Agent, or Firm* — Michael R. Crabb (57) ABSTRACT

An infusion system includes a pump, a fluid delivery line, at least one sensor, a processor, and a memory. The fluid delivery line is connected to the pump for delivering fluid. The at least one sensor is connected to the fluid delivery line for emitting and receiving signals to detect whether there is air in the fluid delivery line. The processor is in electronic communication with the pump and the at least one sensor. The memory is in electronic communication with the processor. The memory comprises programming code for execution by the processor. The programming code is configured to determine a percentage of the air within an observed volume of the fluid delivery line.

12 Claims, 8 Drawing Sheets

◆ DENOTES CRITICAL DIMENSION

| USER AIR VOLUME SETTING (IN μL) | FROTH ALGORITHM (IN μL) | |
|---|---|---|
| | THRESHOLD / OBSERVED VOLUME | |
| | SETTING - 1 | SETTING - 2 |
| 50 | 50uL / 75uL | 50uL / 62.5uL |
| 100 | 100uL / 137.5uL | 100uL / 125uL |
| 150 | 150uL / 200uL | 150uL / 200uL |
| 250 | 250uL / 325uL | 250uL / 325uL |
| 500 | 425uL / 550uL | 425uL / 550uL |

FROTH DETECTION SYSTEM AND METHOD

FIELD OF THE DISCLOSURE

The disclosure relates to a system and method for determining a percentage of air within an observed volume of a fluid delivery line.

BACKGROUND OF THE DISCLOSURE

With intravenous infusion devices, it is necessary to have a robust air detection system to protect the patient from the hazards of air emboli. Several features may be incorporated into an air detection system, allowing the system to be customized to meet the needs of different patient populations. Since air detection is one of the most frequent false alarms in infusion systems, it is necessary that infusion systems can discriminate between conditions that are clinically relevant and those that are not. Most systems employ a single bubble alarm algorithm that detects a single continuous slug of air to prevent air embolism. The ECRI Institute has stated that "We are not aware of any reports of fatal venous air embolism that (have) occurred during the use of pumps having functional air-in-line detectors. This suggests that any detector with minimum volumes within the 0.05 to 0.2 mL range provides sufficient protection from an air embolism." A review of applicable literature confirms this volume as a general guideline to the acceptable amount of air that may safely be absorbed by the body.

Certain circumstances can arise in which a single or continuous slug of air is not present but which is determined or perceived by the clinician to represent an equivalent situation. In particular, when the medication container is emptied during an infusion program, a transition occurs from the delivery of fluid to air. The transition period may involve a mixture of air and fluid ("froth") that does not include a single air slug of sufficient volume to trigger the single bubble alarm. Consequently, delivery of the air/fluid mixture occurs until the single bubble criteria are eventually met. However, the froth that is pumped through the IV line may be (by volume) predominantly air and may be considered by the clinician to be equivalent to a single air slug. In addition, the multitude of small air bubbles comprising froth may coalesce as the mixture approaches the IV patient access point. Consequently, the time period during which froth is pumped prior to a single bubble alarm may be viewed by the clinician as a delay in the alarm due to the observed high percentage of air in the IV infusion line.

An infusion system and method is needed which will provide an alarm trigger which is based upon the percentage of air delivered rather than being based on either a continuous air slug or on a measure of the total air volume delivered through time. This will provide early detection of an empty container condition where froth is present.

SUMMARY OF THE DISCLOSURE

In one embodiment of the disclosure, an infusion system is provided comprising a pump, a fluid delivery line, at least one sensor, a processor, and a memory. The fluid delivery line is connected to the pump for delivering fluid. The at least one sensor is connected to the fluid delivery line for emitting and receiving signals to detect whether there is air in the fluid delivery line. The processor is in electronic communication with the pump and the at least one sensor. The memory is in electronic communication with the processor. The memory comprises programming code for execution by the processor. The programming code is configured to determine a percentage of the air within an observed volume of the fluid delivery line.

In another embodiment of the disclosure, a method for detecting froth in a fluid delivery line of an infusion system is provided. In one step, fluid is pumped through a fluid delivery line over at least one sensor. In another step, signals are emitted and received from the at least one sensor into and from the fluid delivery line. In an additional step, measurements of the signals are processed, using a processor, to determine a percentage of air within an observed volume of the fluid delivery line.

In still another embodiment of the disclosure, a programming code is disclosed. The programming code is stored on a computer readable memory. The programming code is programmed to determine a percentage of air within an observed volume of a fluid delivery line of an infusion system.

These and other features, aspects and advantages of the disclosure will become better understood with reference to the following drawings, description and claims.

BRIEF DESCRIPTION OF THE DRAWINGS

FIG. 8 is one embodiment of a table which may be used by a froth detection algorithm to, based on user selected air volume input settings, set an observed volume and a froth threshold.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Figure 1:
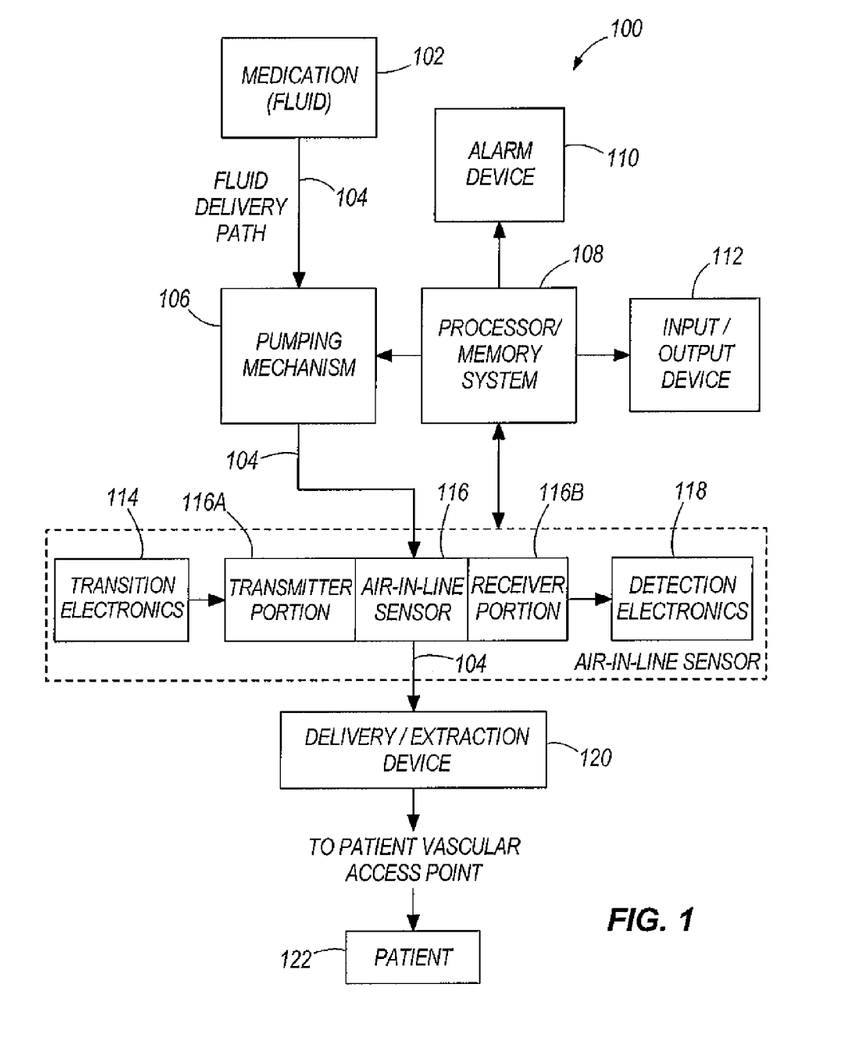
FIG. 1 illustrates a block diagram of a drug delivery infusion system under one embodiment of the disclosure.

FIG. 1 illustrates a block diagram of a drug delivery infusion system 100 under one embodiment of the disclosure. The drug delivery infusion system 100 comprises: a fluid supply container 102; a fluid delivery line 104; a pumping device 106; a processing device 108; an alarm device 110 that generates an audio, visual, or other sensory signal or the like to a user; an input/output device 112; an electronic transmitting device 114; an air-in-line sensor 116; an electronic detection device 118; and a delivery/extraction device 120. The drug delivery infusion system 100 may comprise a drug delivery infusion system such as the Plum A+™, Gemstar™, Symbiq™, or other type of drug delivery infusion system. The fluid supply container 102 comprises a container for delivering fluid such as IV fluid or a drug to the patient 122. The fluid delivery line 104 comprises one or more tubes, connected between the fluid supply container 102, the pumping device 106, the air-in-line sensor 116, and the delivery/extraction device 120, for transporting fluid from the fluid supply container 102, through the pumping device 106, through the air-in-line sensor 116, through the delivery/extraction device 120 to the patient 122. The fluid delivery line 104 may also be used to transport blood, extracted from the patient 122 using the delivery/extraction device 120, through the air-in-line sensor 116 as a result of a pumping action of the pumping device 106. The pumping device 106 comprises a pump for pumping fluid from the supply container 102 or for pumping blood from the patient 122.

The pumping device 106 may comprise a plunger based pump, a peristaltic pump, or another type of pump. The processing device 108 comprises a processor for processing information received from the air-in-line sensor 116 and for executing a software algorithm to determine a percentage of air within an observed volume of the fluid delivery line 104. The processing device 108 includes a computer readable memory, containing programming code for execution by the processor, and a clock. The alarm device 110 comprises an alarm, triggered by the processing device 108, for notifying the clinician (also referred to as 'user' herein) if the percentage of the air within the observed volume of the fluid delivery line 104 exceeds a froth threshold, and for stopping the pumping device 106 prior to an air embolism being delivered through the fluid delivery line 104 and the delivery/extraction device 120 to the patient 122. The input/output device 112 comprises a device which allows a clinician to input or receive information. The input/output device 112 allows a clinician to input information which determines what observed volume and froth threshold settings are applied by the programming code using the processing device 108. The input/output device 112 may allow a clinician to select a user-inputted medication infusion program to be applied by the processing device 108. The input/output device 112 may further output information to the clinician.

The electronic transmitting device 114 comprises electronic circuitry, connected to the air-in-line sensor 116, which transmits a signal from a transmitter portion 116A of the air-in-line sensor 116, through fluid delivery line 104, to a receiver portion 116B of the air-in-line sensor 116 connected to the electronic detection device 118. The air-in-line sensor 116 is connected to the fluid delivery line 104 distal of the pumping device 106. In other embodiments, the air-in-line sensor 116 may be located proximal to the pumping device 106 or may be located in both proximal and distal positions. The transmitter and receiver portions 116A and 116B of the air-in-line sensor 116 sense the presence of air or fluid within the fluid delivery line 104. The transmitter and receiver portions 116A and 116B of the air-in-line sensor 116 comprise a transducer such as an ultrasonic sensor, an acoustic sensor, an optical sensor, or another type of sensor. The electronic detection device 118 comprises electronic circuitry, connected to the receiver portion 116B of the air-in-line sensor 116, for receiving the signal transmitted from the electronic transmitting device 114, through the transmitter portion 116A of the air-in-line sensor 116, through the fluid delivery line 104, to the receiver portion 116B of the air-in-line sensor 116, to the electronic detection device 118. Alternate arrangements of the sensor transmitter and receiver are possible and include both side-by-side arrangements and the use of a single transducer to both transmit and receive a reflected signal. The delivery/extraction device 120 comprises a patient vascular access point device for delivering fluid from the fluid supply container 102 to the patient 122, or for extracting blood from the patient 122. The delivery/extraction device 120 may comprise a needle, a catheter, a cannula, or another type of delivery/extraction device.

Figure 2:
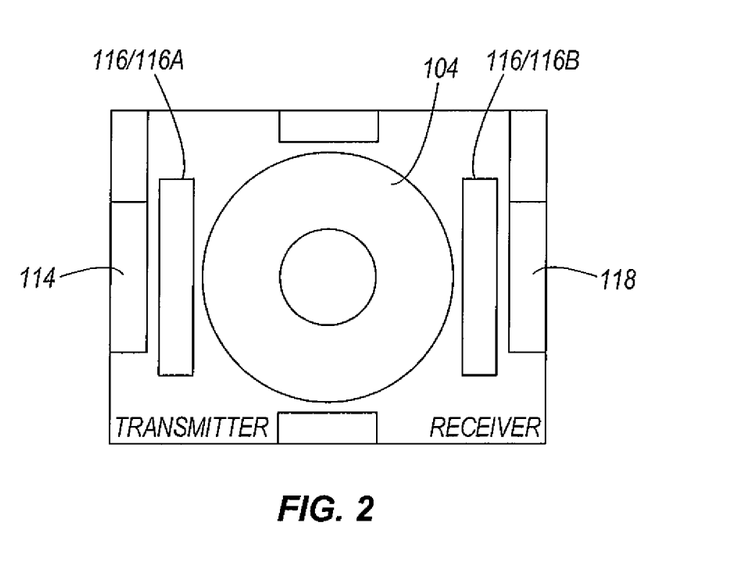
FIG. 2 illustrates a cross-section through one embodiment of a segment of fluid delivery line coupled to an electronic transmitting device, a transmitter portion of an air-in-line sensor, a receiver portion of an air-in-line sensor, and an electronic detection device.

FIG. 2 illustrates a cross-section through one embodiment of a segment of fluid delivery line 104 coupled to the electronic transmitting device 114, the transmitter portion 116A of the air-in-line sensor 116, the receiver portion 116B of the air-in-line sensor 116, and the electronic detection device 118. The transmitter and receiver portions 116A and 116B of the air-in-line sensor 116 comprise piezoelectric crystals compressed against each side of the fluid delivery line 104 creating more surface area for uniform acoustic coupling and better signal to noise ratio. This arrangement of the transmitter and receiver portions 116A and 116B of the air-in-line sensor 116 enables the transmission and detection of an ultrasonic signal through a target volume of the infusion line fluid delivery line 104. The electronic transmitting device 114 generates a nominal 5.25 MHz ultrasonic signal directed from the transmitter 116A portion of the air-in-line sensor 116, through the fluid delivery line 104, to the receiver portion 116E of the air-in-line sensor 116 connected to the electronic detection device 118. When liquid is present in the fluid delivery line 104 at the position of the air-in-line sensor 116, the receiver portion 116B of the air-in-line sensor 116 and the electronic detection device 118 generate a larger electrical signal than when air is present at the same position. Because of an inversion in the electronics of the electronic detection device 118, the software of the processing device 108 will receive a low signal when liquid is present at the location of the air-in-line sensor 116, and a high signal when air is present at the location of the air-in-line sensor 116. When a cassette is loaded into the pumping device 106, the segment of the fluid delivery line 104 distal to the cassette is clamped into place in front of the air-in-line sensor 116. This enables reliable and repeatable sensor performance over multiple cassettes.

Figure 3:
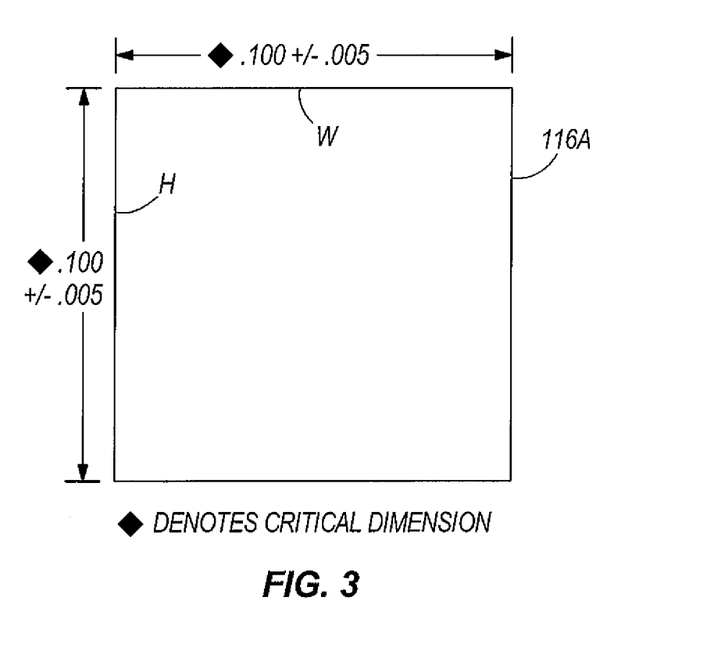
FIG. 3 illustrates a front elevation view of one embodiment of piezoelectric crystals of a transmitter portion of an air-in-line sensor.

FIG. 3 illustrates a top view through one embodiment of the piezoelectric crystals of the transmitter portion 116A of the air-in-line sensor 116 of FIG. 2. As shown, the height H of the air-in-line sensor 116 comprises 0.100 inches and the width W of the air-in-line sensor 116 comprises 0.100 inches. The dimensions of the receiver portion 116B of the air-in-line sensor 116 of FIG. 2 are identical to the transmitter portion 116A of the air-in-line sensor 116 of FIG. 3. In other embodiments, the dimensions of the transmitter and receiver portions 116A and 116B of the air-in-line sensor 116 of FIG. 2 may vary.

The ability of the ultrasonic signal to propagate from the transmitter portion 116A to the receiver portion 116B of the air-in-line sensor 116 of FIG. 2 is governed by the acoustic impedance of the materials. The matching layers of the transducers of the transmitter and receiver portions 116A and 116E are designed to control the amplitude of the reflections at the piezo-matching layer and matching layer-fluid delivery line interfaces. The other significant component of the signal path is the liquid or air inside the fluid delivery line 104. The acoustic impedances (Za)@ 20° C. of interest are as follows: water=1.5×106 kg/(m² s); tubing polymer=3.3×106 kg/(m² s); and air=413.2 kg/(m² s). Reflections of the ultrasonic signal occur at material boundaries and are governed by the differences in acoustic impedance. The reflection coefficient (RC) is defined as: RC=(Za−Za1)/(Za+Za1). A high RC indicates that the signal will not pass through the boundary. For the tubing to water interface, the RC=0.375 which indicates that a majority of the signal will pass through the interface. For the tubing to air interface, the RC=0.999 which indicates that none of the signal will pass through the interface.

The electronic detection device 118A converts the signal received by the receiver portion 116B of the air-in-line sensor 116 back to an electrical signal as governed by the equation: Vout=λ Tpiezo σ/Drvr, where Vout=the electrical signal received by the receiver portion 116B of the air-in-line sensor; λ=the strain on the piezo crystal due to the ultrasonic wave; σ=the stress on the piezo crystal due to the ultrasonic wave; Tpiezo=the thickness of the piezo crystal; and Drvr=the mechanical displacement of the piezo by the ultrasonic crystal. Thus, when fluid is in the fluid delivery line 104, the receiver portion 116B of the air-in-line sensor 116 is able to collect a large amount of ultrasonic energy since, fluid is a better conductor then air. This appears as a low voltage at the A/D converter of the electronic detection device 118 because the signal received by the receiver portion 116B of the air-in-line sensor 116 is inverted electrically. The position of the fluid or air inside the fluid delivery line 104 relative to the transmitter and receiver portions 116A and 116B of the air-in-line sensor 116 also influences the amount of energy the receiver portion 116B of the air-in-line sensor detects. When air is in the fluid delivery line 104, the receiver portion 116B of the air-in-line sensor 116 collects little energy.

Figure 4:
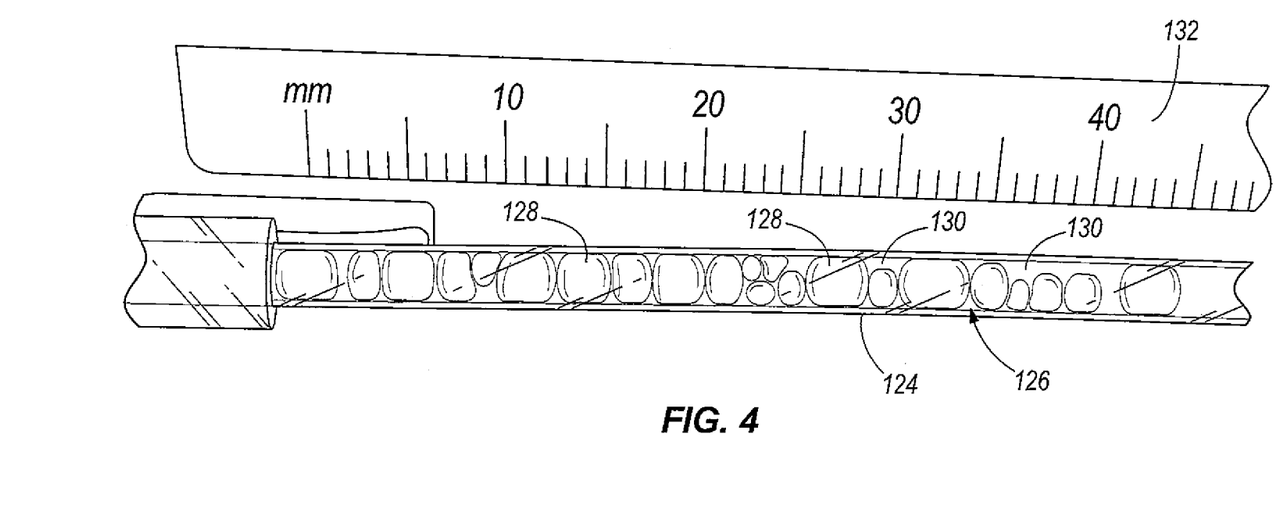
FIG. 4 illustrates a front view of a tube containing froth comprising a mixture of air and liquid.

FIG. 4 illustrates a front view of a tube 124 containing froth 126 comprising a mixture of air 128 and liquid 130. The markings of the ruler 132 adjacent to the tube 124 illustrate that there are only small continuous air bubbles 128 present without the presence of any large continuous air bubble. Although there are only small continuous air bubbles 128 present in the tube 124, there is still a significant amount of air 128 in the tube 124 due to the large number of the air bubbles 128. Due to the large number of the air bubbles 128 in the tube 124, a clinician's perception of the amount of air 128 within the tube 124 may be substantially off-base. This may lead to a clinician being concerned that the air-detection system is not working when in fact it is.

Figure 5:
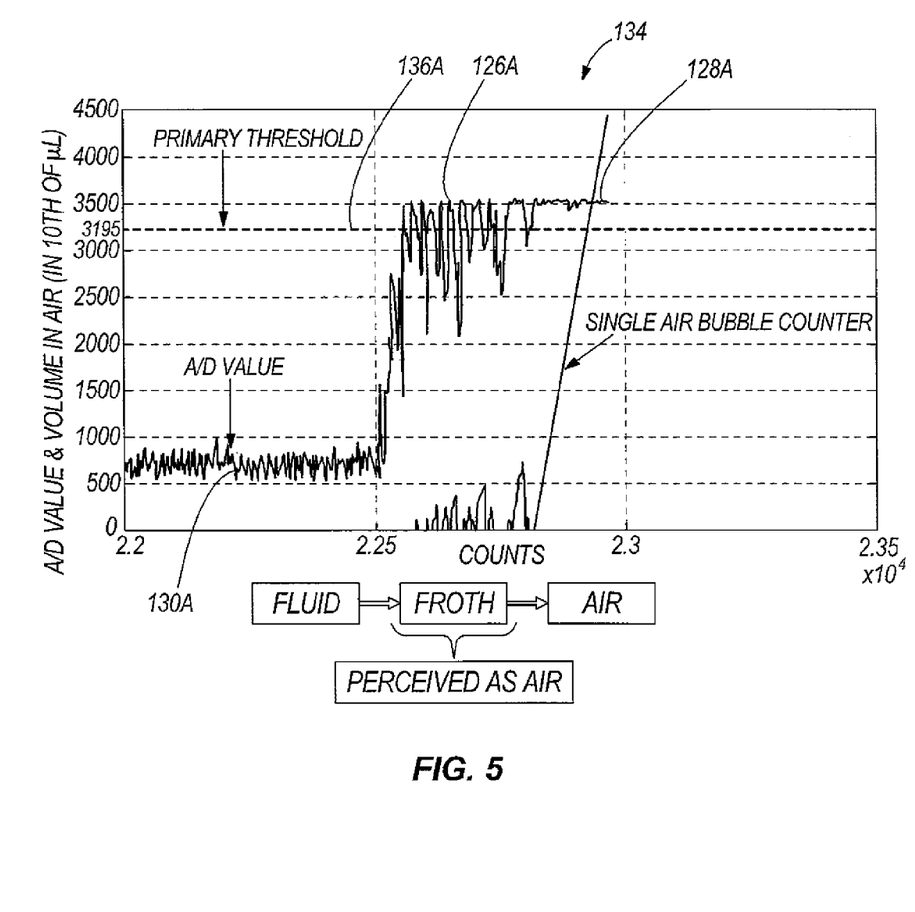
FIG. 5 is a graph plotting exemplary air-sensor ADC readings versus counts for a fluid sample passing by an air-in-line sensor within a fluid delivery line.

FIG. 5 illustrates a graph 134 plotting exemplary air-sensor ADC (also referred to as Analog-to-Digital-Count) readings versus counts for a fluid sample passing by the air-in-line sensor 116 within fluid delivery line 104 of the embodiment of FIG. 1. As shown, the plot contains some areas of fluid 130A having ADC values which stay below the primary air/fluid threshold 136A, some areas of air 128A having ADC values which stay above the primary air/fluid threshold 136A, and some areas of froth 126A having ADC values which fluctuate between being below and being above the primary air/fluid threshold 136A signifying an air/fluid mixture.

Figure 6:
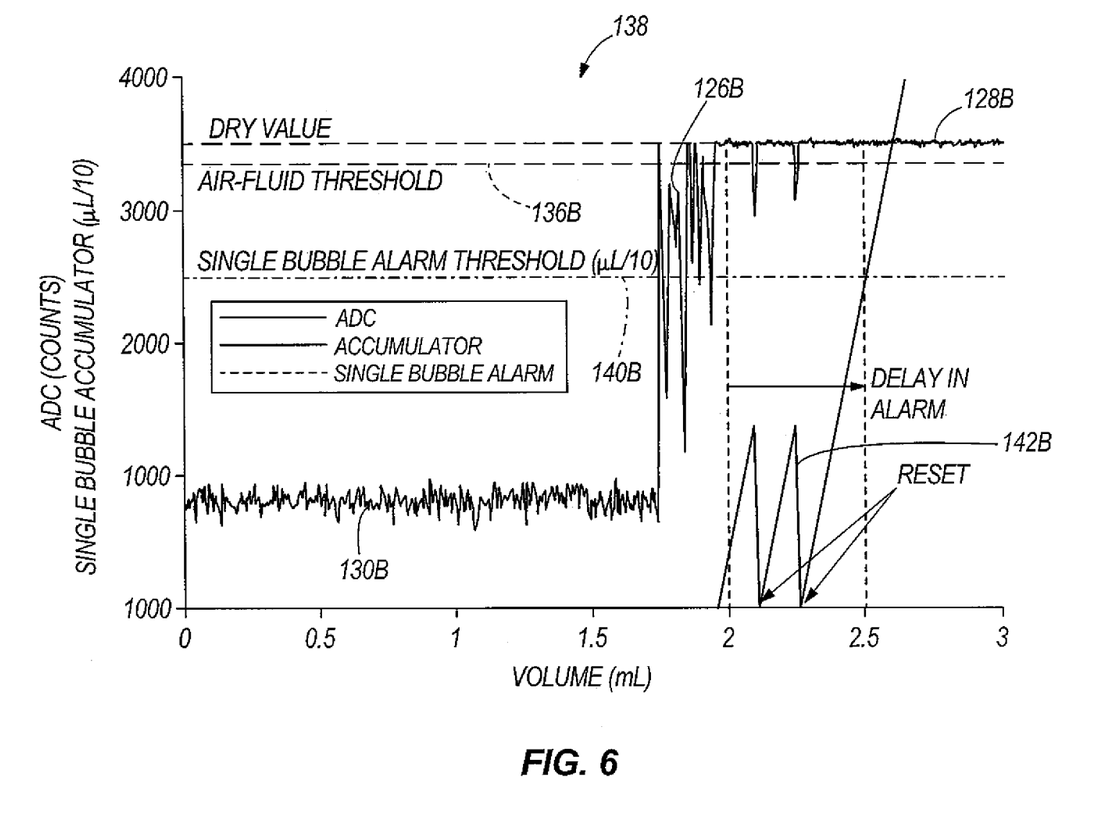
FIG. 6 is a graph plotting exemplary air-sensor ADC values versus volume for another fluid sample passing by an air-in-line sensor within a fluid delivery line.

When froth is present, in many of the existing air detection systems and methods, although an accurate air volume may be detected an alarm may not be generated due to the infusion of fluid interrupting the detection of a single or continuous slug of air. FIG. 6 illustrates a graph 138 plotting exemplary air-sensor ADC values versus volume for another fluid sample passing by the air-in-line sensor 116 within fluid delivery line 104 of the embodiment of FIG. 1. As shown, the plot contains some areas of fluid 130B having ADC values which stay below the primary air/fluid threshold 136B, some areas of air 128B having ADC values which stay above the primary air/fluid threshold 136B, and some areas of froth 126B having ADC values which fluctuate between being below and being above the primary air/fluid threshold 136B signifying an air/fluid mixture. When applying a single bubble threshold 140B, as is typically done in the existing art to signal an alarm for the presence of a single bubble of air over the single bubble threshold 140B, due to the signal fluctuations between liquid and air, the single air-bubble-accumulated value 142B continually gets interrupted until a significant amount of air has passed through the system.

This disclosure determines the percentage of air within an observed volume of a fluid delivery line of an infusion system in order to detect the presence of froth. The froth detection apparatus and process of the disclosure searches a moving window of fluid delivery and declares an alarm if the total air volume detected within that observed volume exceeds a froth threshold. In such manner, the froth detection apparatus and process continually analyzes the percentage of air which is disposed within the moving window at various points in time as the fluid moves through the fluid delivery line and sets off the alarm if at any time the froth threshold within the moving window is exceeded. The amounts of the observed volume and the froth threshold vary and are set by the froth detection algorithm based upon clinician selected input. This may comprise the clinician inputting a selected single bubble air alarm quantity which, based on the clinician input, results in the froth detection algorithm then automatically selecting the observed volume and froth threshold settings to be applied in the froth detection algorithm. In other embodiments, the amounts of the observed volume and the froth threshold may be set during manufacturing.

The froth detection apparatus and process of the disclosure can be applied alone or applied in conjunction with other types of air tests. For instance, the froth detection apparatus and process of the disclosure may be used in conjunction with a single air bubble test or a cumulative air bubble test, both of which are disclosed in U.S. Pat. No. 7,981,082, which is hereby incorporated by reference. In addition or alternatively, the froth detection apparatus and process of the disclosure may be used in conjunction with a stuck-droplet test. The froth detection apparatus and process of the disclosure is equally capable of detecting a single contiguous air bubble and therefore could be used as a replacement for the single air bubble test.

Figure 7:
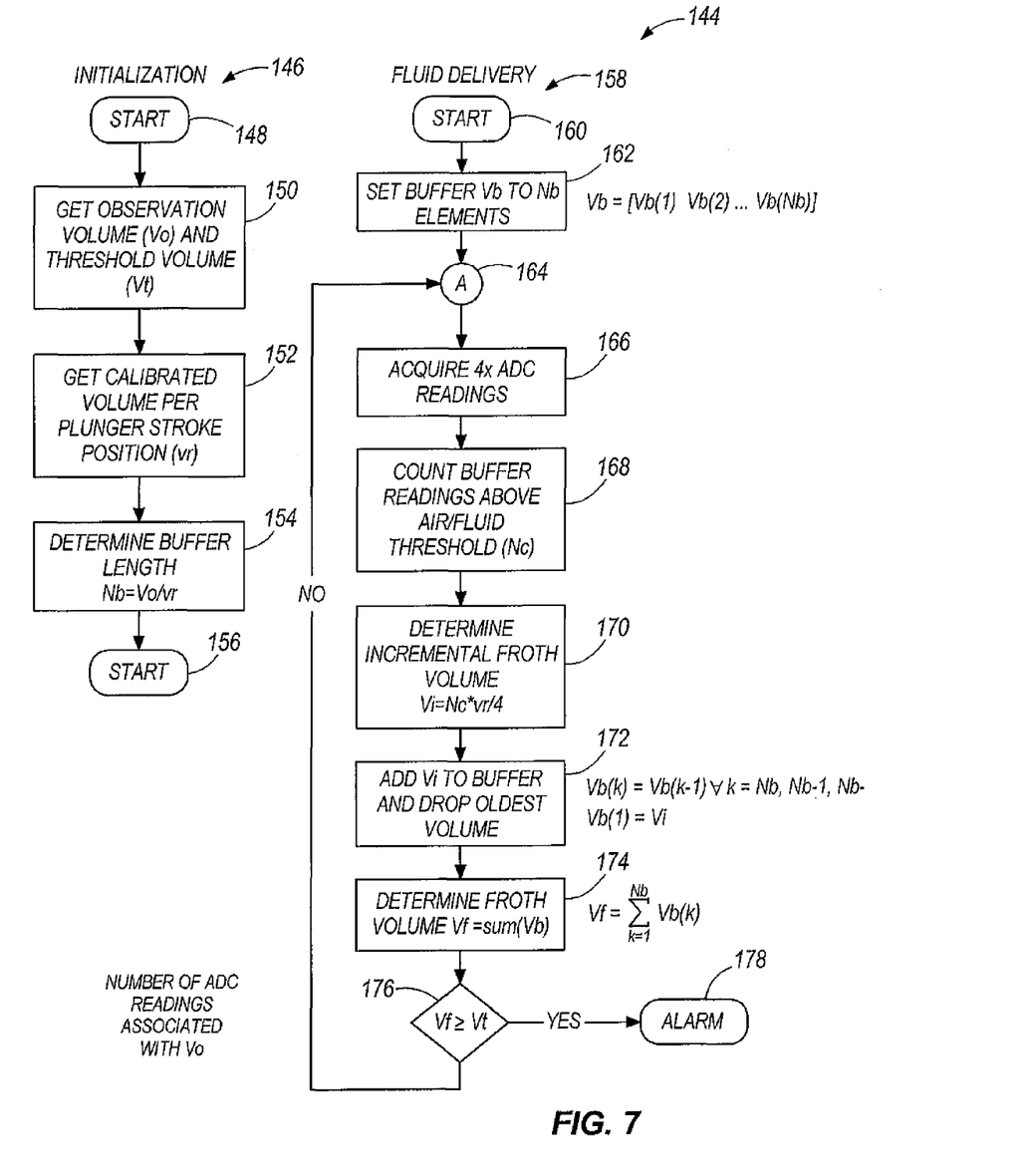
FIG. 7 is a flowchart implementing a froth detection algorithm to detect froth.

FIG. 7 illustrates one embodiment of a flowchart 144 implementing a froth detection algorithm which may be followed to detect froth 126, 126A, 126B, as shown in FIGS. 4, 5, and 6, in fluid delivery line 104 as shown in FIG. 1. The method of the flowchart 144 of FIG. 7 may be implemented using the drug delivery infusion system 100 of FIG. 1. As shown in FIG. 7, the flowchart is split between an initialization state 146 comprising steps 148, 150, 152, 154, and 156, and a fluid delivery state 158 comprising steps 160, 162, 164, 166, 168, 170, 172, 174, 176, and 178. The initialization state 146 occurs prior to the state of a medication infusion. In step 148, the method starts. In step 150 an observation volume (Vo) and froth threshold volume (Vt) are set. In one embodiment, step 150 comprises a clinician selecting an air volume setting at which point the froth detection algorithm automatically selects the observation volume and froth threshold volume settings based on the clinician selected air volume setting.

FIG. 8 illustrates one embodiment of a table 179 which may be used by the froth detection algorithm in step 150 of FIG. 7. Column 180 lists various possible user selected air volume input settings which may be inputted by the user into the input device 112. Columns 182 and 184 lists two different settings which may be applied by the froth detection algorithm to select the observation volume 186 and the froth threshold volume 188 based on the user inputted air volume setting. Column 184 is the preferred setting. Based on the user selected air volume setting 180 and depending on which of the two different settings 182 and 184 have been provided, the froth detection algorithm automatically selects the corresponding observation volume 186 and froth threshold volume 188 to be applied by the froth detection algorithm. For instance, if the froth detection algorithm is programmed to apply setting 184 and if the user inputs an air volume setting 180 of 50 μL, the froth detection algorithm selects a froth threshold volume 188 of 50 μL and an observation volume 186 of 62.5 μL. In other embodiments, various tables, settings, or methods may be utilized by the froth detection algorithm in step 150 to select the observation volume and the froth threshold volume, including any of the settings being set during manufacturing rather than being user-selected.

Referring back to FIG. 7, in step 152 the froth detection algorithm determines a calibrated volume per plunger stroke position (vr). In one embodiment the calibrated volume per plunger stroke position is determined by the froth detection algorithm by dividing the calibrated volume per stroke for the particular model of pump by the total number of plunger stroke positions in one stroke for the particular model of pump. For instance, in a Symbiq™ pump the calibrated volume is 75 μL and the total number of plunger stroke positions is 6. As a result, in a Symbiq™ pump the calibrated volume per plunger stroke position is 75 μL/6=12.5 μL. In other embodiments, the calibrated volume stroke per plunger stroke position (vr) may be determined in different manners.

In step 154 a determination is made by the froth detection algorithm as to the buffer length (Nb). The buffer length (Nb) is a circular buffer that represents a moving window of fluid delivery. In one embodiment of a pump having six plunger positions in a stroke, each element of the buffer represents one-sixth of the calibrated stroke volume. Because the buffer length (Nb) comprises a nominal volume, the number of elements in the buffer is adjusted for any difference between the nominal and calibrated stroke volumes. In one embodiment, the buffer length (Nb) is calculated by dividing the observation volume (Vo) set in step 150 by the calibrated volume per plunger stroke position (vr) determined in step 152. For instance, if the observation volume (Vo) is set to be 62.5 μL in step 150 and if the calibrated volume per plunger stroke position (vr) is determined to be 12.5 μL in step 152, then in step 154 the buffer length (Nb) is calculated to be Vo/vr=62.5 μL/12.5 μL=5. In other embodiments, the buffer length may be calculated in other ways.

In step 156 the initialization state 146 ends and the method proceeds to step 160 of the fluid delivery state 158 which occurs during a medication infusion. In step 160, the fluid delivery state 158 starts. In step 162 the froth detection algorithm sets the buffer element array (Vb) for the buffer length (Nb). For instance, the froth detection algorithm sets the buffer element to be Vb=[Vb(1), Vb(2), . . . Vb(Nb)] with each element Vb(1), Vb(2), . . . Vb(Nb) of the buffer element array Vb being initially set to zero. For instance, if Nb is determined to be 5 in step 154 then Vb=[Vb(1), Vb(2), Vb(3), Vb(4), Vb(5)]=[0, 0, 0, 0, 0]. In other embodiments, the buffer element array may be set in different manners.

Figure 9:
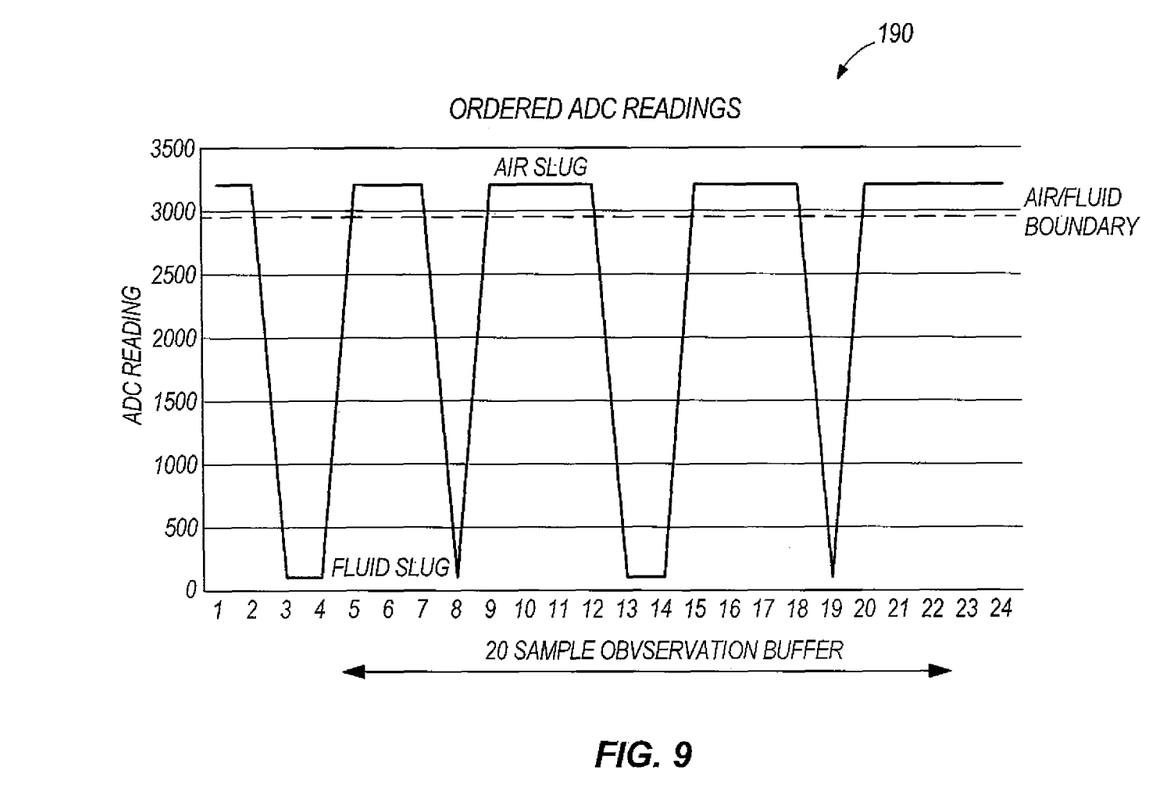
FIG. 9 is a graph plotting exemplary air-sensor ADC values versus counts for still another fluid sample passing by an air-in-line sensor within a fluid delivery line.

The method proceeds through location step 164 to step 166. In step 166, the froth detection algorithm acquires four (4) separate ADC readings at the current plunger stroke position of the pump, delivering the infusion fluid through the fluid delivery line, and saves them in the buffer. FIG. 9 illustrates a graph 190 plotting exemplary air-sensor ADC values versus counts for a fluid sample passing by the air-in-line sensor 116 within fluid delivery line 104 of the embodiment of FIG. 1 for a Symbiq™ pump. Applying step 166 of FIG. 7 to the graph 190 of FIG. 9, at the first plunger position the froth detection algorithm takes four (4) separate ADC readings at counts 1, 2, 3, and 4 which comprise ADC values [3200, 3200, 100, 100] which are subsequently saved in a buffer. In other embodiments, a varying number of ADC readings may be taken at various plunger stroke positions.

In step 168 the froth detection algorithm counts the number of buffer readings for the current plunger stroke position above the air/fluid threshold (Nc). For instance, if the air/fluid threshold is set to be 3,000 and in step 166 the four (4) separate ADC readings for the first plunger stroke position saved in the buffer comprise ADV values [3200, 3200, 100, 100], then step 168 would determine that two (2) of the four (4) separate ADC readings for the first plunger stroke position saved in the buffer are greater than the air/fluid threshold of 3,000. This is determined because the two (2) ADC readings of 3,200 are both greater than the air/fluid threshold of 3,000 but the other two (2) ADC readings of 100 are both less than 3,000. In other embodiments, the air/fluid threshold (Nc) may be determined in different manners.

In step 170 the froth detection algorithm determines the incremental froth volume (Vi) which comprises the volume of air at the current plunger stroke position. The first time the incremental froth volume (Vi) is calculated Vi=V(1) with i=1. In one embodiment, the incremental froth volume (VI) is calculated by multiplying the number of buffer readings at the current plunger stroke position which are above the air/fluid threshold (Nc) by the calibrated volume per plunger stroke position (vr) and dividing the total by the four (4) ADC readings which taken at the current plunger stroke position. This equation is expressed as Vi=Nc*vr/4. For instance, if Nc was determined to be 2 in step 168 and if vr was determined to be 12.5 μL in step 152, then in step 170 Vi would be determined to be Vi=V(1)=Nc*vr/4=2*12.5 μL/4=6.25 μL. In other embodiments, the incremental froth volume (Vi) may be determined in different manners.

In step 172 the froth detection algorithm adds the incremental froth volume (Vi) determined in step 170 to the buffer and drops the oldest incremental froth volume (Vi) from the buffer if it is outside the determined buffer length (Nb) as determined in step 154. This is represented by the equation Vb(k)=Vb(k−1) for all k from Nb, Nb−1, . . . 2 wherein Vb(1)=Vi. For instance, if Nb was determined to be 5 in step 154 and Vi was determined to be Vi=V(1)=6.25 μL in step 170, then in step 172 Vi=V(1)=6.25 μL is added to the buffer and the oldest incremental volume is not dropped from the buffer because, since at this point it's the first time calculating Vi, there have not yet been more than 5 Vi values (the buffer length) saved in the buffer. As a result, the buffer saves the incremental volume array as Vb=[6.25 μL, 0, 0, 0, 0] since only incremental froth volume V(1) has been determined at this point in time.

In step 174 the froth detection algorithm determines the froth volume (Vf) using the equation Vf=sum (Vb)= $\Sigma_{k=1}^{Nb}$Vb(k). For instance, in the instant example, Vf is calculated to be Vf=V(1)+V(2)+V(3)+V(4)+V(5)=6.25 μL+0+0+0+0=6.25 μL since only V(1) has been calculated at this point in time. In other embodiments, the froth volume (Vf) may be calculated using other methods.

In step 176 the froth detection algorithm determines whether the froth volume (Vf) calculated in step 174 is greater than or equal to the froth threshold volume (Vt) determined in step 150. If a determination is made in step 176 that the froth volume (Vf) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. The closed loop comprising steps 164, 166, 168, 170, 172, 174, and 176 is continually repeated until either the froth alarm signals in step 178, or the system is shut-off to stop monitoring froth in the system. In the instant example, in step 176 a determination is made that the froth volume (Vf) is less than the froth threshold volume (Vt) since Vf was determined to be 6.25 μL in step 174 which is less than the Vt determination of 50 μL in step 150. As a result, the method proceeds directly to location step 164 which then proceeds immediately to step 166.

In step 166 for the example, the froth detection algorithm acquires another four (4) separate ADC readings at the second plunger stroke position of the pump, delivering the infusion fluid through the fluid delivery line, and saves them in the buffer. Applying step 166 to the graph 190 of FIG. 9, at the second plunger position the froth detection algorithm takes another four (4) separate ADC readings at counts 5, 6, 7, and 8 which comprise ADC values [3200, 3200, 3200, 100] which are subsequently saved in the buffer.

In step 168 for the example, the froth detection algorithm counts the number of buffer readings above the air/fluid threshold (Nc) for the second plunger stroke position of the pump. For instance, since the air/fluid threshold was set to be 3,000 and in step 166 the four (4) separate ADC readings at the second plunger stroke position saved in the buffer comprise ADV values [3200, 3200, 3200, 100], step 168 determines that three (3) of the four (4) separate ADC readings at the second plunger stroke position saved in the buffer are greater than the air/fluid threshold of 3,000.

In step 170 for the example, the froth detection algorithm determines the incremental froth volume Vi=V(2) which comprises the volume of air at the second plunger stroke position. V(2) is calculated by multiplying the number of buffer readings at the second plunger stroke position which are above the air/fluid threshold (Nc) by the calibrated volume per plunger stroke position (vr) and dividing the total by the four (4) ADC readings taken at the second plunger stroke position. As a result, using the Nc determination of 3 for the second plunger stroke position from step 168 and using the vr determination of 12.5 μL from step 152, V(2) is calculated in step 170 to be V(2)=Nc*vr/4=3*12.5 μL/4=9.375 μL.

In step 172 for the example, the froth detection algorithm adds the incremental froth volume (Vi) determined in step 170 to the buffer and drops the oldest incremental froth volume (Vi) from the buffer if it is outside the determined buffer length (Nb) as determined in step 154. In the instant example, since Nb was determined to be 5 in step 154 and Vi was determined to be Vi=V(2)=9.375 μL in step 170, then in step 172 Vi=V(2)=9.375 μL is added to the buffer and the oldest incremental volume (comprising V(1)=6.25 μL) is not dropped from the buffer because, since at this point it's only the second time calculating Vi, there have not yet been more than 5 Vi values (the buffer length) saved in the buffer. As a result, the buffer saves the incremental volume array as [9.375 μL, 6.25 μL, 0, 0, 0] since only incremental volumes V(1) and V(2) have been calculated at this point in time.

In step 174 for the example, the froth detection algorithm determines the froth volume (Vf) using the equation Vf=sum (Vb)=$\Sigma_{k=1}^{Nb}$Vb(k). For instance, in the instant example, Vf is calculated to be Vf=V(1)+V(2)+V(3)+V(4)+V(5)=6.25 μL+9.375 μL+0+0+0=15.625 μL since only V(1) and V(2) have been calculated at this point in time.

In step 176 for the example, the froth detection algorithm determines whether the froth volume (Vf) calculated in step 174 is greater than or equal to the froth threshold volume (Vt) determined in step 150. If a determination is made in step 176 that the froth volume (Vf) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. In the instant example, in step 176 a determination is made that the froth volume (Vf) is less than the froth threshold volume (Vt) since Vf was determined to be 15.625 μL in step 174 which is less than the Vt determination of 50 μL in step 150. As a result, the method proceeds directly to location step 164, to repeat the closed loop, which then proceeds immediately to step 166.

In step 166 for the example, the froth detection algorithm acquires another four (4) separate ADC readings at the third plunger stroke position of the pump, delivering the infusion fluid through the fluid delivery line, and saves them in the buffer. Applying step 166 to the graph 190 of FIG. 9, at the third plunger position the froth detection algorithm takes another four (4) separate ADC readings at counts 9, 10, 11, and 12 which comprise ADC values [3200, 3200, 3200, 3200] which are subsequently saved in the buffer.

In step 168 for the example, the froth detection algorithm counts the number of buffer readings above the air/fluid threshold (Nc) for the third plunger stroke position of the pump. For instance, since the air/fluid threshold was set to be 3,000 and in step 166 the four (4) separate ADC readings at the third plunger stroke position saved in the buffer comprise ADV values [3200, 3200, 3200, 3200], step 168 determines that four (3) of the four (4) separate ADC readings at the third plunger stroke position saved in the buffer are greater than the air/fluid threshold of 3,000.

In step 170 for the example, the froth detection algorithm determines the incremental froth volume Vi=V(3) which comprises the volume of air at the third plunger stroke position. V(3) is calculated by multiplying the number of buffer readings at the third plunger stroke position which are above the air/fluid threshold (Nc) by the calibrated volume per plunger stroke position (vr) and dividing the total by the four (4) ADC readings taken at the third plunger stroke position. As a result, using the Nc determination of 4 for the third plunger stroke position from step 168 and using the vr determination of 12.5 μL from step 152, V(3) is calculated in step 170 to be V(3)=Nc*vr/4=4*12.5 μL/4=12.5 μL.

In step 172 for the example, the froth detection algorithm adds the incremental froth volume (Vi) determined in step 170 to the buffer and drops the oldest incremental froth volume (Vi) from the buffer if it is outside the determined buffer length (Nb) as determined in step 154. In the instant example, since Nb was determined to be 5 in step 154 and Vi was determined to be Vi=V(3)=12.5 μL in step 170, then in step 172 Vi=V(3)=12.5 μL is added to the buffer and the oldest incremental volume (comprising V(1)=6.25 μL) is not dropped from the buffer because, since at this point it's only the third time calculating Vi, there have not yet been more than 5 Vi values (the buffer length) saved in the buffer. As a result, the buffer saves the incremental volume array as [12.5 μL, 9.375 μL, 6.25 μL, 0, 0] since only incremental volumes V(1), V(2), and V(3) have been calculated at this point in time.

In step 174 for the example, the froth detection algorithm determines the froth volume (Vf) using the equation Vf=sum (Vb)=$\Sigma_{k=1}^{Nb}$Vb(k). For instance, in the instant example, Vf is calculated to be Vf=V(1)+V(2)+V(3)+V(4)+V(5)=6.25 μL+9.375 μL+12.5 μL+0+0=28.125 μL since only V(1), V(2), and V(3) have been calculated at this point in time.

In step 176 for the example, the froth detection algorithm determines whether the froth volume (Vf) calculated in step 174 is greater than or equal to the froth threshold volume (Vt) determined in step 150. If a determination is made in step 176 that the froth volume (Vf) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. In the instant example, in step 176 a determination is made that the froth volume (Vf) is less than the froth threshold volume (Vt) since Vf was determined to be 28.125 μL in step 174 which is less than the Vt determination of 50 μL in step 150. As a result, the method proceeds directly to location step 164, to repeat the closed loop, which then proceeds immediately to step 166.

In step 166 for the example, the froth detection algorithm acquires another four (4) separate ADC readings at the fourth plunger stroke position of the pump, delivering the infusion fluid through the fluid delivery line, and saves them in the buffer. Applying step 166 to the graph 190 of FIG. 9, at the fourth plunger position the froth detection algorithm takes another four (4) separate ADC readings at counts 13, 14, 15, and 16 which comprise ADC values [100, 100, 3200, 3200] which are subsequently saved in the buffer.

In step 168 for the example, the froth detection algorithm counts the number of buffer readings above the air/fluid threshold (Nc) for the fourth plunger stroke position of the pump. For instance, since the air/fluid threshold was set to be 3,000 and in step 166 the four (4) separate ADC readings at the fourth plunger stroke position saved in the buffer comprise ADV values [100, 100, 3200, 3200], step 168 determines that two (2) of the four (4) separate ADC readings at the fourth plunger stroke position saved in the buffer are greater than the air/fluid threshold of 3,000.

In step 170 for the example, the froth detection algorithm determines the incremental froth volume Vi=V(4) which comprises the volume of air at the fourth plunger stroke position. V(4) is calculated by multiplying the number of buffer readings at the fourth plunger stroke position which are above the air/fluid threshold (Nc) by the calibrated volume per plunger stroke position (vr) and dividing the total by the four (4) ADC readings taken at the fourth plunger stroke position. As a result, using the Nc determination of 2 for the second plunger stroke position from step 168 and using the vr determination of 12.5 μL from step 152, V(2) is calculated in step 170 to be V(4)=Nc*vr/4=2*12.5 μL/4=6.25 μL.

In step 172 for the example, the froth detection algorithm adds the incremental froth volume (Vi) determined in step 170 to the buffer and drops the oldest incremental froth volume (Vi) from the buffer if it is outside the determined buffer length (Nb) as determined in step 154. In the instant example, since Nb was determined to be 5 in step 154 and Vi was determined to be Vi=V(4)=6.25 μL in step 170, then in step 172 Vi=V(4)=6.25 μL is added to the buffer and the oldest incremental volume (comprising V(1)=6.25 μL) is not dropped from the buffer because, since at this point it's only the fourth time calculating Vi, there have not yet been more than 5 Vi values (the buffer length) saved in the buffer. As a result, the buffer saves the incremental volume array as [6.25 μL, 12.5 μL, 9.375 μL, 6.25 μL, 0] since only incremental volumes V(1), V(2), V(3), and V(4) have been calculated at this point in time.

In step 174 for the example, the froth detection algorithm determines the froth volume (VI) using the equation Vf=sum (Vb)=$\Sigma_{k=1}^{Nb}$Vb(k). For instance, in the instant example, Vf is calculated to be Vf=V(1)+V(2)+V(3)+V(4)+V(5)=6.25 μL+9.375 μL+12.5+6.25+0=34.375 μL since only V(1), V(2), V(3), and V(4) have been calculated at this point in time.

In step 176 for the example, the froth detection algorithm determines whether the froth volume (Vf) calculated in step 174 is greater than or equal to the froth threshold volume (Vt) determined in step 150. If a determination is made in step 176 that the froth volume (VI) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. In the instant example, in step 176 a determination is made that the froth volume (Vf) is less than the froth threshold volume (Vt) since. Vf was determined to be 34.375 μL in step 174 which is less than the Vt determination of 50 μL in step 150. As a result, the method proceeds directly to location step 164, to repeat the closed loop, which then proceeds immediately to step 166.

In step 166 for the example, the froth detection algorithm acquires another four (4) separate ADC readings at the fifth plunger stroke position of the pump, delivering the infusion fluid through the fluid delivery line, and saves them in the buffer. Applying step 166 to the graph 190 of FIG. 9, at the fifth plunger position the froth detection algorithm takes another four (4) separate ADC readings at counts 17, 18, 19, and 20 which comprise ADC values [3200, 3200, 100, 3200] which are subsequently saved in the buffer.

In step 168 for the example, the froth detection algorithm counts the number of buffer readings above the air/fluid threshold (Nc) for the fifth plunger stroke position of the pump. For instance, since the air/fluid threshold was set to be 3,000 and in step 166 the four (4) separate ADC readings at the fifth plunger stroke position saved in the buffer comprise ADV values [3200, 3200, 100, 3200], step 168 determines that three (3) of the four (4) separate ADC readings at the fifth plunger stroke position saved in the buffer are greater than the air/fluid threshold of 3,000.

In step 170 for the example, the froth detection algorithm determines the incremental froth volume Vi=V(5) which comprises the volume of air at the fifth plunger stroke position. V(5) is calculated by multiplying the number of buffer readings at the fifth plunger stroke position which are above the air/fluid threshold (Nc) by the calibrated volume per plunger stroke position (vr) and dividing the total by the four (4) ADC readings taken at the fifth plunger stroke position. As a result, using the Nc determination of 3 for the fifth plunger stroke position from step 168 and using the vr determination of 12.5 µL from step 152, V(5) is calculated in step 170 to be V(5)=Nc*vr/4=3*12.5 µL 14=9.375 µL.

In step 172 for the example, the froth detection algorithm adds the incremental froth volume (Vi) determined in step 170 to the buffer and drops the oldest incremental froth volume (Vi) from the buffer if it is outside the determined buffer length (Nb) as determined in step 154. In the instant example, since Nb was determined to be 5 in step 154 and Vi was determined to be Vi=V(5)=9.375 µL in step 170, then in step 172 Vi=V(5)=9.375 µL is added to the buffer and the oldest incremental volume (comprising V(1)=6.25 µL) is not dropped from the buffer because, since at this point it's only the fifth time calculating Vi, there have not yet been more than 5 Vi values (the buffer length) saved in the buffer. As a result, the buffer saves the incremental volume array as [9.375 µL, 6.25 µL, 12.5, 9.375, 6.25].

In step 174 for the example, the froth detection algorithm determines the froth volume (Vf) using the equation Vf=sum (Vb)=$\Sigma_{k=1}^{Nb}$Vb(k). For instance, in the instant example, Vf is calculated to be Vf=V(1)+V(2)+V(3)+V(4)+V(5)=6.25 µL+9.375 µL+12.5 µL+6.25 µL+9.375 µL=43.75 µL.

In step 176 for the example, the froth detection algorithm determines whether the froth volume (Vf) calculated in step 174 is greater than or equal to the froth threshold volume (Vt) determined in step 150. If a determination is made in step 176 that the froth volume (Vf) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. In the instant example, in step 176 a determination is made that the froth volume (Vf) is less than the froth threshold volume (Vt) since Vf was determined to be 43.75 µL in step 174 which is less than the Vt determination of 50 µL in step 150. As a result, the method proceeds directly to location step 164, to repeat the closed loop, which then proceeds immediately to step 166.

In step 166 for the example, the froth detection algorithm acquires another four (4) separate ADC readings at the sixth plunger stroke position of the pump, delivering the infusion fluid through the fluid delivery line, and saves them in the buffer. Applying step 166 to the graph 190 of FIG. 9, at the sixth plunger position the froth detection algorithm takes another four (4) separate ADC readings at counts 21, 22, 23, and 24 which comprise ADC values [3200, 3200, 3200, 3200] which are subsequently saved in the buffer.

In step 168 for the example, the froth detection algorithm counts the number of buffer readings above the air/fluid threshold (Nc) for the sixth plunger stroke position of the pump. For instance, since the air/fluid threshold was set to be 3,000 and in step 166 the four (4) separate ADC readings at the sixth plunger stroke position saved in the buffer comprise ADV values [3200, 3200, 3200, 3200], step 168 determines that four (4) of the four (4) separate ADC readings at the sixth plunger stroke position saved in the buffer are greater than the air/fluid threshold of 3,000.

In step 170 for the example, the froth detection algorithm determines the incremental froth volume Vi=V(6) which comprises the volume of air at the sixth plunger stroke position. V(6) is calculated by multiplying the number of buffer readings at the sixth plunger stroke position which are above the air/fluid threshold (Nc) by the calibrated volume per plunger stroke position (vr) and dividing the total by the four (4) ADC readings taken at the sixth plunger stroke position. As a result, using the Nc determination of 4 for the sixth plunger stroke position from step 168 and using the vr determination of 12.5 µL from step 152, V(6) is calculated in step 170 to be V(6)=Nc*vr/4=4*12.5 µL/4=12.5 µL.

In step 172 for the example, the froth detection algorithm adds the incremental froth volume (Vi) determined in step 170 to the buffer and drops the oldest incremental froth volume (Vi) from the buffer if it is outside the determined buffer length (Nb) as determined in step 154. In the instant example, since Nb was determined to be 5 in step 154 and Vi was determined to be Vi=V(6)=12.5 µL in step 170, then in step 172 Vi=V(6)=12.5 µL is added to the buffer and the oldest incremental volume (comprising V(1)=6.25 µL) is dropped from the buffer because, since at this point it's the sixth time calculating Vi, there have been more than 5 Vi values (the buffer length) saved in the buffer. As a result, the buffer saves the incremental volume array as [12.5 µL, 9.375 µL, 6.25 µL, 12.5 µL, 9.375 µL] since incremental volumes V(1)=6.25 µL was dropped from the buffer.

In step 174 for the example, the froth detection algorithm determines the froth volume (Vf) using the equation Vf=sum (Vb)=$\Sigma_{k=1}^{Nb}$Vb(k). For instance, in the instant example, Vf is calculated to be Vf=V(1)+V(2)+V(3)+V(4)+V(5)=9.375 µL+12.5 µL+6.25 µL+9.375 µL+12.5 µL=50 µL.

In step 176 for the example, the froth detection algorithm determines whether the froth volume (Vf) calculated in step 174 is greater than or equal to the froth threshold volume (Vt) determined in step 150. If a determination is made in step 176 that the froth volume (Vf) is greater than or equal to the froth threshold volume (Vt) then the method proceeds directly to step 178 and a froth alarm is set-off to indicate that too much froth is in the system. However, if a determination is made in step 176 that the froth volume (Vf) is less than the froth threshold volume (Vt) then the method proceeds directly to location step 164 which then proceeds immediately to step 166. In the instant example, in step 176 a determination is made that the froth volume (Vf) is greater than or equal to the froth threshold volume (Vt) since Vf was determined to be 50 µL in step 174 which is greater than or equal to the Vt determination of 50 µL in step 150. As a result, for the example, the method proceeds directly to step 178 and a froth alarm is set-off indicating that too much froth is present in the system. In other embodiments, one or more steps of the method may be done out of the recited order, modified or not followed, or additional steps may be added.

In another embodiment of the disclosure, the air sensor signal is subject to an adaptive/dynamic threshold. An alarm condition occurs when the number of air sensor readings in a particular volume exceeds a percentage of the entire volume. The percentage can be user set or automatically updated according to the programmed infusion drug type via a user customizable and downloadable drug library or hard coding in the pumping device of the infusion system. In one embodiment, a bubble detection filter is applied that converts the series of ADC measurements into a binary sequence in which each non-zero value represents air. The filter operates on the basis of the observed signal variance through time rather than the absolute value. The fluid variance is estimated such that s(k)=standard deviation of all air sensor values that are non-air. The average fluid level is estimated such that m(k)=average of all values that are non-air or a set of N recent values such that N represents ADC measurements for a volume that is equal to or greater than the user set observation volume, V. Nominally, N is set to 60 readings. A dynamic threshold is provided such that $T(k)=m(k)+C\,s(k)$, wherein C is a constant, nominally set to three, used to define the confidence interval associated with air sensor variability when fluid is observed. For any given sample, K the ADC voltage is determined as either air or fluid according to $T(k)$, wherein $T(k)$ is initially set to a nominally high value (150 counts less than the calibrated air reading). Consequently, $T(k)$ represents an adaptive threshold that provides sensitivity or improved air/fluid discrimination when micro-bubbles or stuck droplets are present on the sensor. The detection of perceived volume is performed as a percentage of a user set maximum air volume, Vo, or the number of observations collected during the infusion of Vo as determined based on the volume associated with each measurement (vr) according to $Nb=Vo/vr$. For example, the parameter, P, defines the percentage threshold of acceptable air in a particular volume, Vo, where both P and Vo are constants for a given infusion program. Then, if the number of air events detected in a sliding window of observations exceeds the number of observations equal to $P*Vo/vr$, an alarm is generated. In the case in which particular fluids are known to develop "froth", the value for P can be set automatically by drug type. For example, in the case of saline, P may be set at a level of 90% due to low incidence of froth while albumin may have a percentage value as low as 50%.

Another embodiment of the disclosure involves the use of a measurement weighted up-down counter. Many of the previously reported up-down counters are threshold dependent and involve incrementing the detected volume of air by a certain amount when the measured ADC voltage exceeds a specific and fixed level. The volume increment is chosen to reflect the estimated or known volume associated with the measurement under consideration. Conversely, when the measured ADC voltage is below the fixed threshold, the volume is decremented by the total volume associated with the measurement or a fraction thereof. When the total volume, $V(k)$, exceeds a level set by the user or software (e.g., 500 uL), an alarm condition occurs. The problem with this prior approach is that the presence of froth may produce intermediate values that are below the fixed threshold, indicating a partial air observation. For example, a given ADC measurement may reflect an average value through time in which both air and fluid were observed and result in a voltage level that is between the expected values for fluid and air.

To overcome this issue, in one embodiment of the disclosure incrementing is weighted according to the probability of the presence of fluid or air. For instance, in one embodiment the programming code may be configured to analyze a plurality of ADC readings taken by at least one sensor to determine what measurement-weighted number, which is weighted by a weighting factor to account for a confidence level that the particular ADC reading comprises either air or fluid, of the plurality of ADC readings exceeds an air-fluid threshold. In another embodiment, this weighting factor, $w(k)$, may be directly proportional to the measured air sensor voltage, $v(k)$, as follows: $w(k)=\min(1.0, (v(k)-vmin)/(vmax-vmin)-0.5)$, wherein k is the sample measurement index, $\min(\,)$ is the minimum function, vmax is the calibrated value for air (e.g., 3000), and vmin is the calibrated value for fluid (e.g., 500). The volume, $V(k)$, may be incremented as follows: $V(k)=V(k)+w(k)\,Vf$, wherein Vf is the air or fluid volume associated with $V(k)$. In another embodiment, $w(k)$ may be calculated directly from the probability that a given measurement is associated with air or water based on Bayesian statistics, fuzzy logic, empirical rules, or other methods. Regardless of the method used, the incremented value is weighted positively or negatively according to the confidence that a particular ADC measurement is either air or fluid respectively. In other embodiments, various incrementing methods may be used to accommodate for the confidence level that a particular ADC measurement is either air or fluid respectively.

One or more embodiments of the disclosure overcome one or more issues of the existing art by providing an alarm trigger in an infusion system which is based upon the percentage of air delivered rather than being based on either a continuous air slug or being based on a measure of the total air volume delivered through time. This alarm trigger provides early detection of an empty container condition where froth is present.

It should be understood, of course, that the foregoing relates to exemplary embodiments of the disclosure and that modifications may be made without departing from the scope of the disclosure as set forth in the following claims.

We claim:
1. An infusion system comprising:
   a pump;
   a fluid delivery line connected to the pump for delivering fluid;
   at least one sensor connected to the fluid delivery line for emitting and receiving signals to detect whether there is air in the fluid delivery line;
   a processor in electronic communication with the pump and the at least one sensor; and
   a memory in electronic communication with the processor, wherein the memory comprises programming code for execution by the processor, and the programming code is configured to determine a partial/percentage volume of the air within an observed volume of the fluid delivery line, by analyzing a plurality of analog-to-digital count readings taken by the at least one sensor to determine in what total number of the plurality of the analog-to-digital count readings a froth exceeded an air-fluid threshold, and by multiplying the total number of the plurality of the analog-to-digital count readings in which the froth exceeded the air-fluid threshold by a calibrated volume per analog-to-digital count reading to determine the partial/percentage volume within the observed volume that the froth exceeded the air-fluid threshold, and is configured to generate an alarm if the partial/percentage volume exceeds an alarm limit.

2. The infusion system of claim 1 wherein the alarm limit comprises a froth threshold.

3. The infusion system of claim 2 wherein the memory comprises a plurality of saved pair settings comprising different froth thresholds for different observed volumes, and the programming code is configured to accept a user input which determines which of the saved pair settings is applied by the programming code.

4. The infusion system of claim 1 wherein the programming code is configured to determine a dynamic froth threshold, and is configured to generate the alarm if the partial/percentage volume exceeds the dynamic froth threshold.

5. The infusion system of claim 1 wherein the observed volume comprises a window of a set volume, wherein the programming code is configured to continually analyze the partial/percentage volume within the observed volume of the fluid delivery line which is disposed within the window at various points in time as the fluid moves through the fluid delivery line.

6. The infusion system of claim 1 wherein the programming code is configured to analyze the plurality of analog-to-digital count readings taken by the at least one sensor to determine what measurement-weighted number, which is weighted by a weighting factor to account for a confidence level that the particular analog-to-digital count reading comprises either the air or the fluid, of the plurality of the analog-to-digital count readings exceed the air-fluid threshold.

7. A method for detecting froth in a fluid delivery line of an infusion system comprising:
pumping fluid through a fluid delivery line over at least one sensor;
emitting and receiving signals from the at least one sensor into and from the fluid delivery line to detect whether there is air in the fluid delivery line;
processing measurements of the signals, using a processor, to determine a partial/percentage volume within an observed volume of the fluid delivery line, to analyze, with the processor, a plurality of analog-to-digital count readings taken by the at least one sensor, to determine, with the processor, in what total number of the plurality of analog-to-digital count readings a froth exceeded an air-fluid threshold, and to multiply, with the processor, the total number of the plurality of the analog-to-digital count readings in which the froth exceeded the air-fluid threshold by a calibrated volume per analog-to-digital count reading to determine the partial/percentage volume within the observed volume that the froth exceeded the air-fluid threshold; and
generating an alarm if the partial/percentage volume exceeds an alarm limit.

8. The method of claim 7 wherein the alarm limit comprises a froth threshold.

9. The method of claim 8 further comprising the processor processing a user input and determining, based on the user input, which of a plurality of saved pair settings, comprising different froth thresholds for different observed volumes, will be used by the processor to determine the partial/percentage volume within the observed volume that the froth exceeded the air-fluid threshold.

10. The method of claim 7 further comprising the processor determining a dynamic froth threshold and triggering the alarm if the partial/percentage volume within the observed volume that the froth exceeded the air-fluid threshold exceeds the dynamic froth threshold.

11. The method of claim 7 further comprising the processor continually analyzing the partial/percentage volume within the observed volume, comprising a window of a set volume, at various points in time as the fluid moves through the fluid delivery line.

12. The method of claim 7 further comprising the processor analyzing the plurality of analog-to-digital count readings taken by the at least one sensor to determine what measurement-weighted number, which is weighted by a weighting factor to account for a confidence level that the particular analog-to-digital count reading comprises either the air or the fluid, of the plurality of the analog-to-digital count readings exceed the air-fluid threshold.

* * * * *